United States Patent [19]
Arbin

US005862908A
[11] Patent Number: 5,862,908
[45] Date of Patent: Jan. 26, 1999

[54] PACKAGING CASE FOR CONDOMS

[75] Inventor: Christian Arbin, Orleans, France

[73] Assignee: Distrilook, Paris, France

[21] Appl. No.: 815,833

[22] Filed: Mar. 12, 1997

Related U.S. Application Data

[63] Continuation of PCT/FR95/01166, Sep. 12, 1995.

[51] Int. Cl.[6] .............................. A45C 11/00; B65D 85/16
[52] U.S. Cl. ................................. 206/69; 206/37; 206/38; 220/339
[58] Field of Search .................................. 206/69, 459.5, 206/37, 38, 216, 223, 461, 467, 470, 471, 807; 220/337–339, 524; 128/842, 844

[56] References Cited

U.S. PATENT DOCUMENTS

| | | | |
|---|---|---|---|
| 1,412,943 | 4/1922 | Kennedy | 220/524 |
| 2,829,765 | 4/1958 | Burger | 206/37 |
| 4,289,232 | 9/1981 | Seibel et al. | 206/69 |
| 4,408,692 | 10/1983 | Sigel et al. | 206/69 |
| 4,569,438 | 2/1986 | Sheffler | 206/37 |
| 4,825,686 | 5/1989 | Marsh | 206/37 |
| 4,892,188 | 1/1990 | Meadows . | |
| 5,316,019 | 5/1994 | Jones | 206/69 |
| 5,437,286 | 8/1995 | Stratton | 206/69 |
| 5,437,383 | 8/1995 | Stull | 220/339 |
| 5,479,940 | 1/1996 | Babled | 206/69 |

FOREIGN PATENT DOCUMENTS

| | | |
|---|---|---|
| 381058 | 8/1907 | France . |
| 8703116 | 8/1987 | Germany . |
| 9004545 | 5/1990 | WIPO . |

*Primary Examiner*—Paul T. Sewell
*Assistant Examiner*—Luan K. Bui
*Attorney, Agent, or Firm*—Oppendahl & Larson

[57] ABSTRACT

A single-use, sealed and tamper-proof condom packaging is formed from an integrally-molded body and a cover connected with a lateral hinge. The body has an annular groove for insertion of the rolled portion of the condom whose terminal cap inserted between the cover and the central stiffening boss, after which the peripheral welding bead is formed.

20 Claims, 2 Drawing Sheets

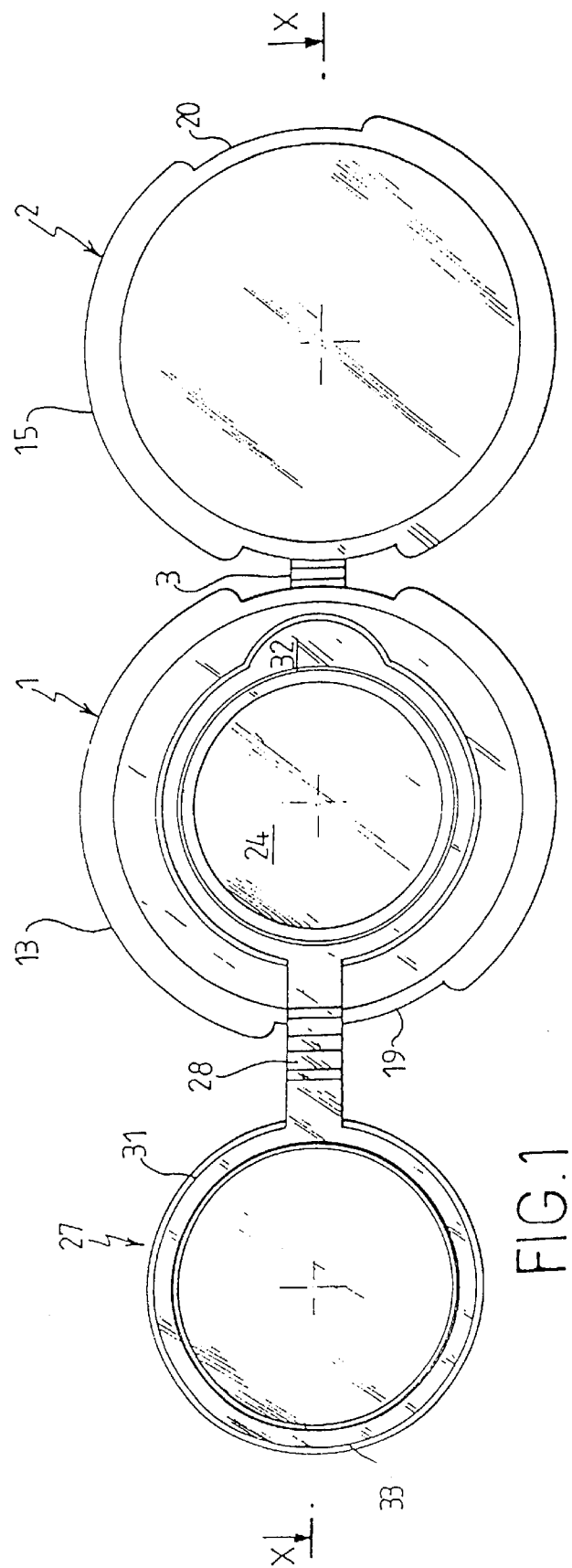
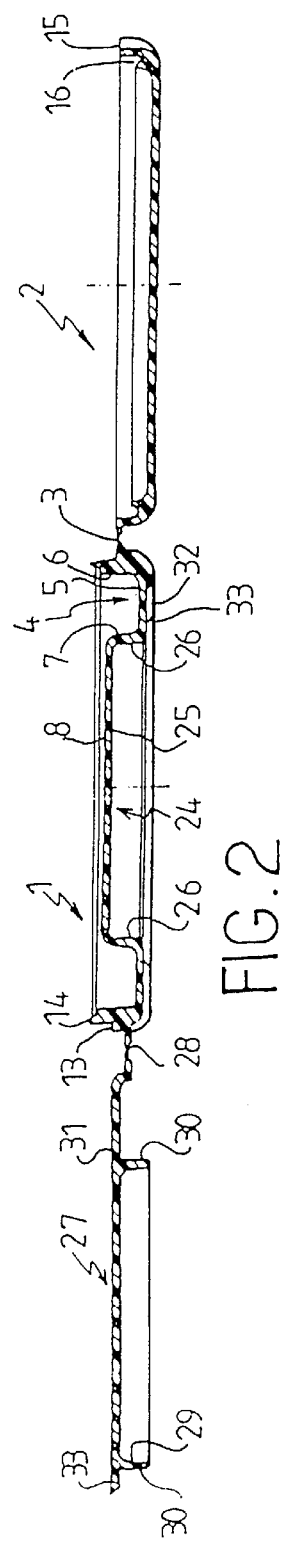

PACKAGING CASE FOR CONDOMS

This application is a continuation of PCT Patent Application No. PCT/FR95/01166 filed Sep. 12, 1995 designating the United States, which is incorporated herein by reference.

BACKGROUND OF THE INVENTION

The present invention relates to a tight, tamper-resistant and non-reusable packaging case for condoms.

Known condom packaging materials are primarily bags consisting of two composite foils facing one another, both of which generally have an aluminum base and plastic material and which are heat-sealed around each condom, preferably along rectilinear weld lines perpendicular to each other.

All of these unit packaging bags have one or more of the following drawbacks:

Their tightness depends on the pressure exerted against their wall by any sharp object;

Maintenance of the integrity of the latex from which the condom if formed depends also on the proximity of any sharp object, but above all on the precautions taken in tearing open the composite foils and extracting the condom in such a way that the latter does not come in contact with the aluminum or metal foil;

In the case of bags, which are by far the most common form of packaging, the condom is removed in an arbitrary fashion, either in the "good" direction which makes it possible to take hold of it by the reservoir—hereinafter referred to as "cap"—in order to expel the air directly, or in the reverse direction, which involves an additional tedious manipulation as well as errors of usage, causing stains on the outer surface of the condom;

Also, in the case of bags, current production methods do not permit centering the trade name on the heat-sealed product, nor the placement of legally required labeling on the material;

The cost of some packaging is very high.

The object of the present invention is to remedy the aforementioned drawbacks by providing a condom packaging case whose tightness and strength provide good preservation of the condom under all circumstances; which, when opened, releases the condom in the "good" direction so that one can take hold of it by expelling the air through simple pressure of the thumb and index finger and without any risk of deterioration of the latex; which makes it possible to center any imprint on its two faces; and which is of low cost.

SUMMARY OF THE INVENTION

The condom packaging in accordance with the invention is a tight, tamper-resistant and non-reusable case. The case comprises a body and a cover connected by a lateral joint, formed from a plastic material and integrally molded together. The body has formed therein an annular recess having a base, an outer wall of slight taper and an inner wall of high taper terminated by a central stiffening boss. The annular recess is designed to house the torus of the condom, with the inner wall of high taper supporting the inner surface of the condom that connects the torus of the condom with the latter's terminal cap. The cap is accommodated between the boss and the cover when the case is in the closed position.

The body of the condom case in accordance with the invention advantageously has an outwardly projecting peripheral edge and a peripheral lip projecting above the annular recess and surrounding the latter. In this case, the cover also has an outwardly projecting peripheral edge and a peripheral groove of the same diameter as the lip which is designed to cooperate with the latter to form a fine tight peripheral weld line during the closing operation of the case, said peripheral edges being separated by a short distance when the case is in the closed position.

In a further embodiment of the invention, the body has a cylindrical basin formed in the bottom surface, delimited by the lower face of the central boss and the inner surface of the inner wall of the annular recess. A lid designed to close the basin is connected to the body by a second integrally-molded lateral joint. The lid preferably has a peripheral lip projecting perpendicularly from the inner surface of the lid and having a slight undercut on its outer face, while the inner peripheral face of the basin is perpendicular to the local surface of the boss and also has a slight undercut, said two undercuts cooperating in order that the closing of the basin by the lid be effected with firm inter-locking to form a sealed reservoir.

According to a preferred embodiment, the closed case has the appearance of a circular disk having plane and parallel faces surrounded in a rounded outer toroidal member.

BRIEF DESCRIPTION OF THE DRAWINGS

FIG. 1 is a plain view of a preferred embodiment of the case according to the invention, integrally molded;

FIG. 2 is a cross-sectional view along the plane of symmetry X—X of the case shown in FIG. 1;

In these figures, the same reference numbers denote the same elements.

DETAILED DESCRIPTION OF THE INVENTION

Figure 3:
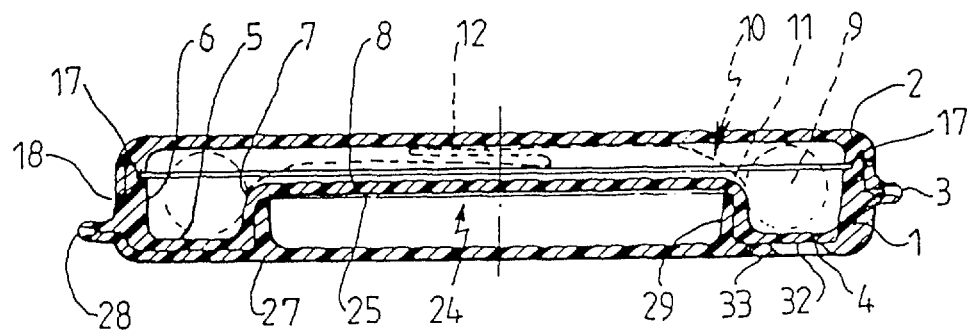
FIG. 3 shows, on an enlarged scale, a cross-sectional view along the same axis of the closed case and containing a condom represented schematically.
Figure 4:
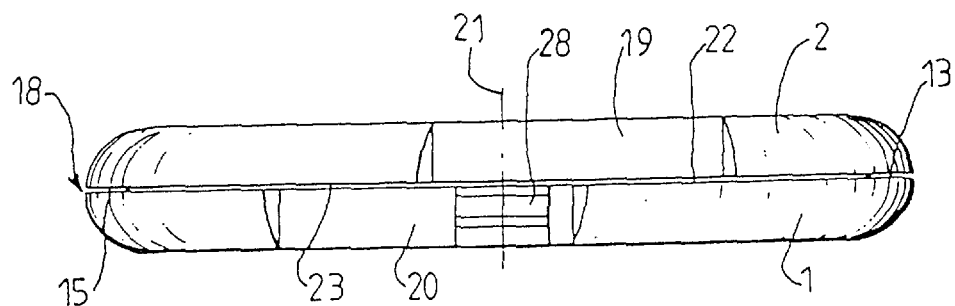
FIG. 4 is a front view of the closed case shown in FIG. 3.
Figure 5:
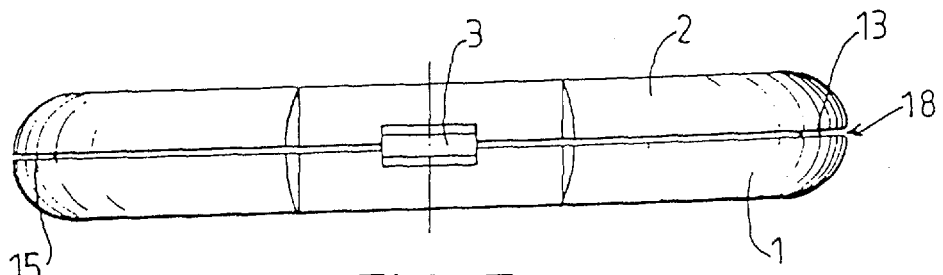
FIG. 5 is a rear view of the closed case shown in FIG. 3.

Referring to all these figures together, the condom packaging case according to the invention is of the tight, tamper-resistant and non-reusable type.

According to a preferred embodiment of the invention, the case comprises, in particular, a body 1 and a cover 2 connected by a lateral joint 3, these three components consisting of a plastic material, preferably a polypropylene- or polyethylene-based plastic, and being integrally molded together.

The body 1 comprises an annular recess 4 having a base 5, an outer wall 6 of slight taper, and an inner wall 7 which is inclined or has a high taper and is terminated by a central stiffening boss 8. The annular recess 4 is designed to accommodate the torus 9 of a condom 10, as will be explained in detail below.

The inner conical wall 7 of high taper is designed to support the inner surface 11 of the condom, which connects the torus 9 with the terminal cap 12 of said condom, the cap 12 being situated between the boss 8 and the cover 2 when the case is in the closed position.

Actually, the inclination of the inner wall 7 and the dimensions of the annular recess 4 are designed in such a way that said wall 7 freely supports the torus 9 of the condom via its inner surface 11, said torus thus being floatingly suspended in the annular recess 4.

Under these conditions, when the cover 2 is abruptly lowered onto the body 1 during one of the production-line operations, the air contained in the cap 12 is violently expelled around the central boss 8 and its peripheral flow can take place freely, first between the inner surface 11 of the condom and the inner wall 7, then between the floating torus 9 and the base 5, as well as the outer wall 6 of the annular recess 4, without thereby resulting any lateral displacement of said torus 9 with respect to said annular recess 4.

In accordance with another feature of the invention, the body 1 comprises an outwardly projecting peripheral edge 13 in the prolongation of said body 1 and a peripheral lip 14 projecting above the annular recess 4 and surrounding the latter, while the cover 2 comprises a peripheral edge 15 projecting outwardly in the prolongation of said cover 2 and a peripheral groove 16 of the same diameter as the lip 14 of the body 1. It is obvious that the lip 14 and the associated groove 16 may be linked in a tight manner by any heating or adhesive means, and the groove may even be replaced by a second projecting lip exactly opposite the lip 14 to form the tight and tamper-resistant receptacle designed for the condom.

However, according to a preferred embodiment of the invention, the groove 16 of the cover 2 is designed to cooperate with lip 14 of the body 1 to form a thin and tight peripheral weld line 17 during the operation of closing the case, so as to make the latter not only tight but also tamper-resistant, as indicated above.

According to a preferred method of operation, the cover 2 is subjected to the vibrations produced by an ultrasonic head while the body 1 remains fixed, which causes a highly localized temperature rise and the formation of the aforementioned weld seam 17 without any risk of deterioration of the latex of the torus 9 situated near-by, as might be the case with other modes of welding.

In the present case, it may be considered that the ultrasonic welding is of the spot/reverse spot type, the groove 16 being capable of presenting a reentrant angle of about 90° and the lip 14 a salient angle of about 60°, the opening of the angle of groove 16 permitting a better flow of the fusing material. However, studies which led to invention have shown that it was equally desirable to consider on the tip of lip 14 a small outwardly projecting lateral part (not shown) and play upon the flexibility of the lip in order to obtain a better weld seam.

It should be noted that when the case is welded as indicated above, the peripheral edges 13 and 15 remain separated by a short distance 18. Preferably, each of the two outwardly projecting edges has an integrally molded part that is undercut toward the interior, the undercut parts 19 and 20 of the two edges 13 and 15, respectively, being arranged essentially opposite the lateral joint 3, at the same distance from the axis of symmetry 21 of the case passing through said joint 3, and symmetrically with respect to this axis 21.

As a result, the non-undercut parts situated opposite the undercut parts 19 and 20 form two separate miters 22 and 23 symmetrical with respect to the axis 21. These miters constitute a possible means of opening the case by permitting to tear the weld seam 17 and separate the cover 2 from the body 1 against the resistance of said weld seam 17, thereby making the case non-reusable. In effect, if it contains a condom and is not welded or closed in a manner other than indicated, the case can no longer close in a normal fashion due to the fact that the latex of the terminal cap 12 and the air present in the latter offer an elastic resistance to any closing pressure and cause the separation of the cover 2 from the body 1 as soon as this pressure is no longer applied.

According to another feature of the invention, the fact of separating the cover 2 from the body 1 during the first opening of the case by tearing the adhesive strip or tight welding seam 17, makes the terminal cap 12 rise up, thereby making it possible to immediately take hold of said cap 12 in the "good" direction in order to expel the air from it before use. Moreover, the outer part of the terminal cap 12 is normally lubricated before the operations of closing and welding the case; the lubricant may be, e.g., one based on alimentary silicone.

According to yet another embodiment of the invention, the body 1 comprises a cylindrical basin 24 delimited by the lower face 25 of the central boss 8 and the inner face 26 of the inner wall 7 of the annular recess 4, and comprises a lid 27 designed to close the basin 24, as well as a second lateral joint 28 connecting the lid 27 with the body 1 and integrally molded with the latter.

The lid 27 comprises a peripheral lip 29 projecting perpendicularly to the local surface of the lid 27 and having a slight undercut on its outer surface 30, while the inner peripheral surface 26 of the basin 24 is perpendicular to the local surface of the boss 8 and also has a slight undercut, these two undercuts cooperating in order that the closing of basin 24 by the lid 27 take place with firm interlocking in order to form a sealed complementary reservoir.

This reservoir may contain, e.g., either a thin folded hygienic bag designed to receive the condom after use, or a complementary lubricating gel which may or may not be aromatized or may or may not be colored.

Moreover, the lid 27 preferably comprises a thin peripheral edge 31 projecting outwardly in the prolongation of said lid and whose part opposite the second joint 28, at least, is beveled and cooperates with a small concave zone 32 arranged on the edge of the basin 24 to form a miter 33 of separation of the lid 27 from the basin 24. Obviously, other means of opening the complementary reservoir may be considered.

When closed, the case advantageously has an ellipsoid or hyperboloid-of-revolution shape in which the boss 8 may be plane, convex or concave.

However, according to a preferred embodiment, the closed case simply has the general shape of a circular disk of planar and parallel faces connected by a rounded external surface of the toric type. Likewise, by preference, the peripheral edges 13 and 15 of the body 1 and the cover 2, which are separated by a short distance 18, are generally planar.

Moreover, the boss 8 is preferably plane, so that the basin 24 forms, with the lid 27, a right cylindrical reservoir.

According to another characteristic of the invention, the lid 27 does not project from the surface of the body 1, and, consequently, a label indicating tamper-resistance of the reservoir may be stuck both on said surface and on the lid. This label will preferably include the complete directions for use with all the legally required indications.

By contrast, the lid 2 of the case may be used as an advertising medium for a stuck-on label or for a presentation obtained by stamping or otherwise. Apart from its obvious commercial interest, such advertising will lead the user to open the case in the "good" direction, i.e., with the advertisement and hence cover 2 above and with the directions-for-use label and, hence, lid 27 and the complementary reservoir below. Under these conditions, the user will have no difficulty in taking hold of the condom 10 by its terminal cap 12 to expel the air from it before use.

Moreover, a number of cases according to the invention may be molded on a mass scale in a known manner, then separated from each other by elimination of the sprues and other external elements. Furthermore, each of the three basic members connected by the two joints 3 and 28, i.e. the cover 2, the body 1 and the lid 27, may have a face situated in a plane (not shown) common to these three members.

The present invention has been described and represented only for explanatory purposes and by no means in a limitative sense, and any useful modification may be brought to it, particularly in the area of equivalent techniques, without exceeding its scope.

I claim:

1. A tamper-resistant, non-reusable packaging for a condom having an outer rolled portion, a terminal cap and a connecting portion extending between the outer rolled portion and the terminal cap, said packaging comprising a body and a cover and a lateral joint integrally formed from a plastic material, wherein the body has a central stiffening boss surrounded by an annular recess, said annular recess having a base, an outer wall and an inner wall and being sized to accommodate the outer rolled portion of the condom whereby the inner wall supports the inner surface of the connecting portion and the terminal cap is accommodated between the boss and the cover when the case is in the closed position, and the outer wall of the annular recess has a slight taper and the inner wall of the annular recess has a high taper so as to freely support the inner surface of the connecting portion and the outer rolled portion of the condom, said outer rolled portion thus being floatingly suspended in the annular recess in such a way that when the cover is abruptly lowered onto the body, air contained in the terminal cap is expelled around the central boss and flows freely, first between the inner surface of the condom and the inner wall of the annular recess and then between the floating outer rolled portion of the condom and the base and the outer wall of the annular recess.

2. The packaging according to claim 1, wherein the body comprises an outwardly projecting peripheral edge and a peripheral lip projecting above and surrounding the annular recess, the cover comprises an outwardly projecting peripheral edge and a peripheral groove of the same diameter as the lip for cooperatively receiving the lip to form a thin tight peripheral weld seam when the packaging is closed, said peripheral edges being separated by a short distance when the case is in the closed position.

3. The packaging according to claim 2, wherein each of the two outwardly projecting peripheral edges has an integrally molded part undercut toward the interior, the undercut parts of the two edges being arranged substantially opposite the lateral joint at the same distance from an axis of symmetry of the case passing through said joint and symmetrically with respect to said axis, the non-undercut parts situated opposite said undercut parts forming two miters symmetrical with respect to said axis and designed for opening the case against the opposition of the weld seam.

4. The packaging according to claim 1, wherein the case, when closed, has the general shape of a circular disk having faces that are planar and parallel and surrounded by a rounded toroidal member.

5. The packaging according to claim 1, wherein the cover of the case is used as an advertising medium.

6. The packaging according to claim 1, further comprising a condom disposed within the packaging, wherein the body is sealed to the cover.

7. The packaging according to claim 6, wherein the body is ultrasonically welded to the cover.

8. A tamper-resistant, non-reusable packaging for a condom having an outer rolled portion, a terminal cap and a connecting portion extending between the outer rolled portion and the terminal cap, said packaging comprising a body and a cover and a lateral joint integrally formed from a plastic material, wherein the body has a central stiffening boss surrounded by an annular recess, said annular recess having a base, an outer wall and an inner wall and being sized to accommodate the outer rolled portion of the condom whereby the inner wall supports the inner surface of the connecting portion and the terminal cap is accommodated between the boss and the cover when the case is in the closed position, and the outer wall of the annular recess has a slight taper and the inner wall of the annular recess has a high taper so as to freely support the inner surface of the connecting portion and the outer rolled portion of the condom, said outer rolled portion thus being floatingly suspended in the annular recess in such a way that when the cover is abruptly lowered onto the body, air contained in the terminal cap is expelled around the central boss and flows freely, first between the inner surface of the condom and the inner wall of the annular recess and then between the floating outer rolled portion of the condom and the base and the outer wall of the annular recess;

wherein the body comprises an outwardly projecting peripheral edge and a peripheral lip projecting above and surrounding the annular recess, the cover comprises an outwardly projecting peripheral edge and a peripheral groove of the same diameter as the lip for cooperatively receiving the lip to form a thin tight peripheral weld seam when the packaging is closed, said peripheral edges being separated by a short distance when the case is in the closed position;

wherein each of the two outwardly projecting peripheral edges has an integrally molded part undercut toward the interior, the undercut parts of the two edges being arranged substantially opposite the lateral joint at the same distance from an axis of symmetry of the case passing through said joint and symmetrically with respect to said axis, the non-undercut parts situated opposite said undercut parts forming two miters symmetrical with respect to said axis and designed for opening the case against the opposition of the weld seam; and wherein the body has formed therein an exterior cylindrical basin delimited by the lower face of the central boss and by the inner surface of the inner wall of the annular recess, and further comprising a lid for closing the basin, the body and the lid being connected by a second lateral joint integrally molded with the lid.

9. The packaging according to claim 8, wherein the lid comprises a peripheral lip projecting perpendicularly from the inner surface of the lid and having a slight undercut on its outer surface, while the inner peripheral surface of the basin is perpendicular to the inner surface of the boss and also has a slight undercut, these two undercuts cooperating to provide a firm interlocking of the lid and the basin so as to form a sealed reservoir.

10. The packaging according to claim 9, wherein the lid comprises a thin outwardly projecting peripheral edge, of which at least the part opposite the second joint is beveled and cooperates with a small concave zone arranged on the edge of the basin to form a miter of separation of the lid from the basin.

11. The packaging according to claim 8, wherein the lid does not project from the surface of the body, and a label indicating tamper resistance of the reservoir may be stuck both on said surface and on the lid.

12. The packaging according to claim 8, wherein the boss is planar and the basin forms with the lid a right cylindrical reservoir.

13. The packaging according to claim 8, wherein the case, when closed, has the general shape of a circular disk having faces that are planar and parallel and surrounded by a rounded toroidal member.

14. The packaging according to claim 8, further comprising a condom disposed within the packaging, wherein the body is sealed to the cover.

15. The packaging according to claim 14, wherein the body is ultrasonically welded to the cover.

16. A tamper-resistant, non-reusable packaging for a condom having an outer rolled portion, a terminal cap and a connecting portion extending between the outer rolled portion and the terminal cap, said packaging comprising a body and a cover and a lateral joint integrally formed from a plastic material, wherein the body has a central stiffening boss surrounded by an annular recess, said annular recess having a base, an outer wall and an inner wall and being sized to accommodate the outer rolled portion of the condom whereby the inner wall supports the inner surface of the connecting portion and the terminal cap is accommodated between the boss and the cover when the case is in the closed position, and the outer wall of the annular recess has a slight taper and the inner wall of the annular recess has a high taper so as to freely support the inner surface of the connecting portion and the outer rolled portion of the condom, said outer rolled portion thus being floatingly suspended in the annular recess in such a way that when the cover is abruptly lowered onto the body, air contained in the terminal cap is expelled around the central boss and flows freely, first between the inner surface of the condom and the inner wall of the annular recess and then between the floating outer rolled portion of the condom and the base and the outer wall of the annular recess;

wherein the body has formed therein an exterior cylindrical basin delimited by the lower face of the central boss and by the inner surface of the inner wall of the annular recess, and further comprising a lid for closing the basin, the body and the lid being connected by a second lateral joint integrally molded with the lid.

17. The packaging according to claim 16, wherein the body comprises an outwardly projecting peripheral edge and a peripheral lip projecting above and surrounding the annular recess, the cover comprises an outwardly projecting peripheral edge and a peripheral groove of the same diameter as the lip for cooperatively receiving the lip to form a thin tight peripheral weld seam when the packaging is closed, said peripheral edges being separated by a short distance when the case is in the closed position.

18. The packaging according to claim 16, wherein the case, when closed, has the general shape of a circular disk having faces that are planar and parallel and surrounded by a rounded toroidal member.

19. The packaging according to claim 16, further comprising a condom disposed within the packaging, wherein the body is sealed to the cover.

20. The packaging according to claim 19, wherein the body is ultrasonically welded to the cover.

* * * * *

UNITED STATES PATENT AND TRADEMARK OFFICE
CERTIFICATE OF CORRECTION

| | |
|---|---|
| PATENT NO. | : 5,862,908 |
| APPLICATION NO. | : 08/815833 |
| DATED | : January 26, 1999 |
| INVENTOR(S) | : Christian Arbin |

It is certified that error appears in the above-identified patent and that said Letters Patent is hereby corrected as shown below:

On the Title page,

Item [74], "Oppendahl" should read -- Oppedahl --

Signed and Sealed this

Eighteenth Day of May, 2010

David J. Kappos
*Director of the United States Patent and Trademark Office*